United States Patent
Mickle et al.

(10) Patent No.: US 6,615,074 B2
(45) Date of Patent: Sep. 2, 2003

(54) APPARATUS FOR ENERGIZING A REMOTE STATION AND RELATED METHOD

(75) Inventors: Marlin Mickle, Pittsburgh, PA (US); Dimitry Gorodetsky, Pittsburgh, PA (US); Leonid Mats, Pittsburgh, PA (US); Lorenz Neureuter, Lancaster, PA (US); Minhong Mi, Pittsburgh, PA (US); Carl Taylor, Pittsburgh, PA (US); Chad Emahizer, Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 158 days.

(21) Appl. No.: 09/951,032

(22) Filed: Sep. 10, 2001

(65) Prior Publication Data

US 2003/0032993 A1 Feb. 13, 2003

Related U.S. Application Data

(63) Continuation-in-part of application No. 09/218,322, filed on Dec. 22, 1998, now Pat. No. 6,289,237.

(51) Int. Cl.$^7$ ............................................. A61B 5/0402
(52) U.S. Cl. ................... 600/509; 343/718; 340/573.1; 128/903
(58) Field of Search ................................. 600/509, 300, 600/308; 607/31–33, 60, 61; 128/903; 343/895, 718, 893, 700 MS; 340/572.7, 573.1

(56) References Cited

U.S. PATENT DOCUMENTS 4,129,125 A  12/1978  Lester et al.
4,166,470 A   9/1979  Nuemann (List continued on next page.)

OTHER PUBLICATIONS

Rao, An Overview of Bulk Scattered Radio Frequency Identification System (RFID) IEEE (1999).

(List continued on next page.)

Primary Examiner—Jeffrey R. Jastrzab
(74) Attorney, Agent, or Firm—Arnold B. Silverman; Eckert Seamans Cherin & Mellott, LLC

(57) ABSTRACT

Apparatus for remote interaction with an object of interest includes a remote station for obtaining information from the object of interest, a base station for transmitting energy in space to and communicating with the remote station and the remote station having conversion means for energizing the remote station responsive to receipt of the transmitted energy. The energy may be of any suitable type including RF power, light, acoustic, magnetic energy or other form of space transmitted or "radiant" energy. The remote station does not have to contain a source of stored energy or a wired connection to a source of energy. The remote station receives the energy transmission and data transmission from the base station and transmits data to the base station. Microprocessor controllers may be provided for the base station and the remote station. The remote station may receive information from sensors and through one or more transponders sequentially communicate information to the base station. An associated method is provided. In other embodiments which are suited for use in miniaturized electronic chip systems, power enhancement and increased effective antenna size are provided. An electronic article containing a microchip having at least one antenna structured to communicate with an antenna remotely disposed with respect to the microchip formed therein and an associated method are provided.

55 Claims, 13 Drawing Sheets

U.S. PATENT DOCUMENTS

| | | |
|---|---|---|
| 4,308,870 A | 1/1982 | Arkans |
| 4,356,825 A | 11/1982 | Veth |
| 4,432,363 A | 2/1984 | Kakegawa |
| 4,443,730 A | 4/1984 | Kitamura et al. |
| 4,494,553 A | 1/1985 | Sciarra et al. |
| 4,576,179 A | 3/1986 | Manus et al. |
| 4,724,427 A | 2/1988 | Carroll |
| 4,857,893 A | 8/1989 | Carroll |
| 4,889,131 A | 12/1989 | Salem et al. |
| 5,022,402 A | 6/1991 | Schieberl et al. |
| 5,230,342 A | 7/1993 | Bobo, Jr. et al. |
| 5,335,551 A | 8/1994 | Ohnishi et al. |
| 5,387,259 A | 2/1995 | Davidson |
| 5,586,555 A | 12/1996 | Bobo, Jr. et al. |
| 5,729,572 A | 3/1998 | Oh |
| 5,736,937 A | 4/1998 | McGirr et al. |
| 5,760,558 A | 6/1998 | Popat |
| 5,768,696 A | 6/1998 | Law |
| 5,808,760 A | 9/1998 | Gfeller |
| 5,815,807 A | 9/1998 | Osmani et al. |
| 5,841,122 A | 11/1998 | Kirchhoff |
| 5,844,516 A | 12/1998 | Vijanen |
| 5,862,803 A | 1/1999 | Besson et al. |
| 5,874,723 A | 2/1999 | Hasegawa et al. |
| 6,289,237 B1 * | 9/2001 | Mickle et al. ............. 600/509 |
| 6,373,447 B1 | 4/2002 | Rostoker et al. |

OTHER PUBLICATIONS

Hornby, RFID Solutions for the Express Parcel and Airline Baggage Industry, Texas Instruments, Limited (Oct. 7, 1999).

* cited by examiner

APPARATUS FOR ENERGIZING A REMOTE STATION AND RELATED METHOD

CROSS REFERENCE TO RELATED APPLICATION

The present application is a continuation-in-part of U.S. application Ser. No. 09/218,322 filed Dec. 22, 1998, now U.S. Pat. No. 6,289,237.

BACKGROUND OF THE INVENTION

1. Field of the Invention

This invention relates to apparatus and an associated method for energizing a remote station through energy transmitted in space and, more specifically, it relates to such a system wherein data with respect to an object of interest may be obtained by the remote station and transmitted to the base station upon interrogation by the base station.

2. Description of the Prior Art

It has long been known in various applications to monitor conditions of a physical system or a patient and provide information in the nature of real-time readouts of certain conditions. Such systems typically have been connected by a suitable wire to a source of electricity at the desired voltage such as line current or batteries.

It has also been known to provide such systems in the medical environment in respect of monitoring characteristics such as patient respiration, heart beat, electrocardiograms and temperature, for example. See, generally, U.S. Pat. Nos. 4,129,125; 4,308,870; 4,443,730; 4,889,131; and 5,335,551.

It has also been known in the medical environment to monitor physiological parameters by employing sensors, a battery powered system, and digital processing means to effect comparison between the measured conditions and stored values and displaying the results. See U.S. Pat. No. 4,356,825.

U.S. Pat. Nos. 5,230,342 and 5,586,555 disclose blood pressure monitors employing a pressurizable pressure transducing bladder with particular emphasis on measuring blood pressure in a supraorbital artery.

U.S. Pat. No. 4,576,179 discloses the use of a chest motion transducer and associated heart rate monitoring apparatus. Cooperating electronics are provided. Alarm means may be triggered under appropriate conditions of the individual being monitored or an indication that the battery voltage has fallen below a preset level. There is an allusion to making provision for short range radio transmission of the signals to remote monitoring stations. See also U.S. Pat. No. 5,022,402.

U.S. Pat. No. 4,494,553 discloses a battery powered respiratory and cardiac monitor wherein a pair of inductance coils are employed along with VHF/FM transmission of signals.

It has been known to suggest the use of a wireless communication link between a base station and transponders in a radio frequency identification system employing modulated back-scattered waves separate attachment of an antenna to a tag integrated current is disclosed. See Rao, an overview of Bulk Scattered Radio Frequency Identification System (RFID) I EEE (1999).

It has been suggested to employ a silicon chip in a transponder having a change pump on voltage doubler current. Hornby, RFID Solutions for the express parcel and airline baggage industry, Texas Instruments, Limited (Oct. 7, 1999).

In spite of the foregoing known systems, there remains a need for a remote unit usable in various environments and at various distances from the base station which remote unit will be adapted to be remotely energized so as not to require hard wired systems or batteries on the remote unit. There is also lacking such systems wherein the remote unit may be miniaturized so as to have numerous potential uses.

SUMMARY OF THE INVENTION

The present invention has met the above-described needs. In the present invention, apparatus for remote interaction with an object of interest includes a remote station for obtaining information from the object of interest and a base station for transmitting energy in space to the remote station and communicating with the remote station. The remote station has conversion means for energizing the remote station by employing the transmitted energy. The base station may transmit the energy as RF power, light, acoustic, magnetic, or in other suitable forms of space transmitted or "radiant" energy.

A power supply is provided for energizing the base station with first antenna means being provided on the base station and second antenna means being provided on the remote station. Sensor means or other information providing means permits the remote station when energized by the base station to transmit information to the base station regarding the object of interest and certain conditions of the remote station. This may be done in real-time. The remote station may be provided with a plurality of transponders each of which may be interrogated by the base station sequentially to provide separate informational packets.

A method of the present invention provides for remote interaction with an object of interest, including providing the remote station and a base station operatively associated therewith, with energy being transmitted in space from the base station to the remote station, and the energy so transmitted being converted by the remote station into electrical power to energize the remote station.

The remote station may be provided with a plurality of transponders each of which will be a source of different information from the other.

The system eliminates the need for batteries on the remote station or the use of hard wired systems.

The invention also provides systems which employ voltage or power enhancing units on the remote station. When employed on electronic chips, antennas having a greater effective area than physical area may be employed advantageously.

The system is adapted for use on system on a chip (SOC) miniaturized unit.

It is object of the present invention to provide a remote station which is adapted to provide information to a base station when interrogation by the base station is initiated.

It is another object of the present invention to provide such a system wherein the remote station is not required to contain an energy storage device, such as a battery, or to be part of a hard wired or printed circuit system.

It is a further object of the present invention to provide such a system wherein energy transmitted in space, such as RF power or light, will be converted into DC power or AC power on the remote station to operate the remote station.

It is a further object of the present invention to provide such a system wherein RF power may be employed to initiate operation of the remote station regardless of whether light is present.

It is a further object of the present invention to provide such a remote station which will transmit dynamic real-time measurements to a base station.

It is another object of the present invention to provide such a system wherein the remote station may be miniaturized and does not require frequent maintenance.

It is another object of the present invention to provide such systems wherein enhanced energy harvesting on a remote station is provided.

It is a further object of the present invention to provide such a system wherein use on miniaturized Systems on a Chip (SOC) is facilitated.

It is yet another object of the present invention to provide such systems wherein the effective antenna area exceeds the physical antenna area.

It is a further object of the present invention to provide such systems which may be employed effectively in Radio Frequency IDentification (RFID) devices.

It is a further object of the present invention to provide such a system wherein the remote station may have a plurality of passive intelligent transponders.

These and other objects of the invention will be more fully understood from the following description of the invention on reference to the accompanying drawings.

DESCRIPTION OF THE PREFERRED EMBODIMENTS

As employed herein, the term "object of interest" means any animate or inanimate item from which information is to be obtained by the remote station.

As employed herein, the term "in space" means that energy or signals are being transmitted through the air or similar medium regardless of whether the transmission is within or partially within an enclosure, as contrasted with transmission of electrical energy by a hard wired or printed circuit boards.

As employed herein, the term "patient" means members of the animal kingdom including humans.

Figure 1:
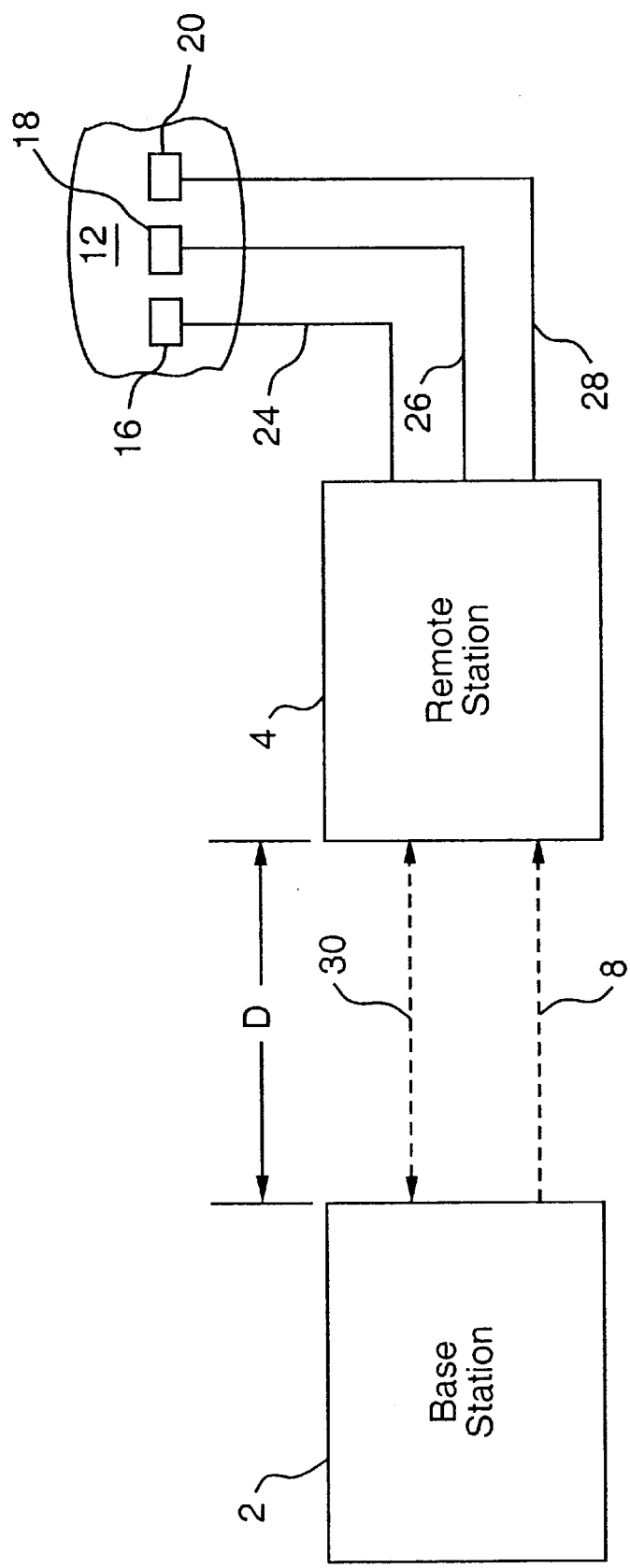
FIG. 1 is a schematic illustration of a form of the present invention showing a base station, a remote station, and a plurality of information providing sensors.

Referring to FIG. 1, there is shown a schematic illustration of the apparatus of the present invention which facilitates remote measurement and/or sensing. A base station 2 is within communication distance D of a remote station 4. In a manner to be described hereinafter, the base station 2 transmits energy which may be RF power, light, acoustic, magnetic or other suitable forms of space transmitted or "radiant" energy, for example, and is indicated generally by the dashed line 8 to remote station 4. Within the remote station 4, the received energy is converted into DC power which serves to operate the remote station 4. In the form illustrated, an object of interest 12 has a plurality of sensors 16, 18, 20 operatively associated therewith, and delivering sensor readings over lines 24, 26, 28, respectively, to the remote station 4 which, in turn, in a manner to be described herein, transmits data through space as indicated by double-headed arrow 30 to base station 2. The power delivered to remote station 4 may also energize sensors 16, 18, 20 through wires 24, 26, 28. The RF energy may also be employed to energize sensors 16, 18, 20 without wires 24, 26, 28. The distance D will vary in accordance with design parameters of the system and may, depending upon the application, be a few millimeters, several feet, or several light years. Dashed arrow 30 also shows data being transmitted from base station 2 to remote station 4.

One of the advantages of the present invention is that the source of power for the remote station 4 is the base station 2 and, therefore, there is no need for hard wiring or printed circuit physical connections with remote station 4. There is also no need for remote station 4 to carry an electrical storage device such as a battery. As a result, activation and powering of the remote station 4 will be achieved through activation of the base station 2. As a result, there will be no need for periodic maintenance on the remote station 4 in order to check battery strength and replace the battery or other power source. This also facilitates the remote station being encapsulated within a suitable protective material, such as a resinous plastic. Homopolymers (including thermoplastic polymers), elastomers and silicon dioxide, for example, are suitable materials for such purposes. Further, this facilitates miniaturization of the remote station and placing the remote station in functionally desirable locations which need not be readily accessible. The remote station, for example, could be implanted in a patient.

It will be appreciated that the remote station 4 can be interrogated by the base station 2, for example, to provide through the remote station 4 a reading of an electronic or mechanical sensor, such as 16, 18, 20 which is operatively associated with the remote station 4.

Figure 2:
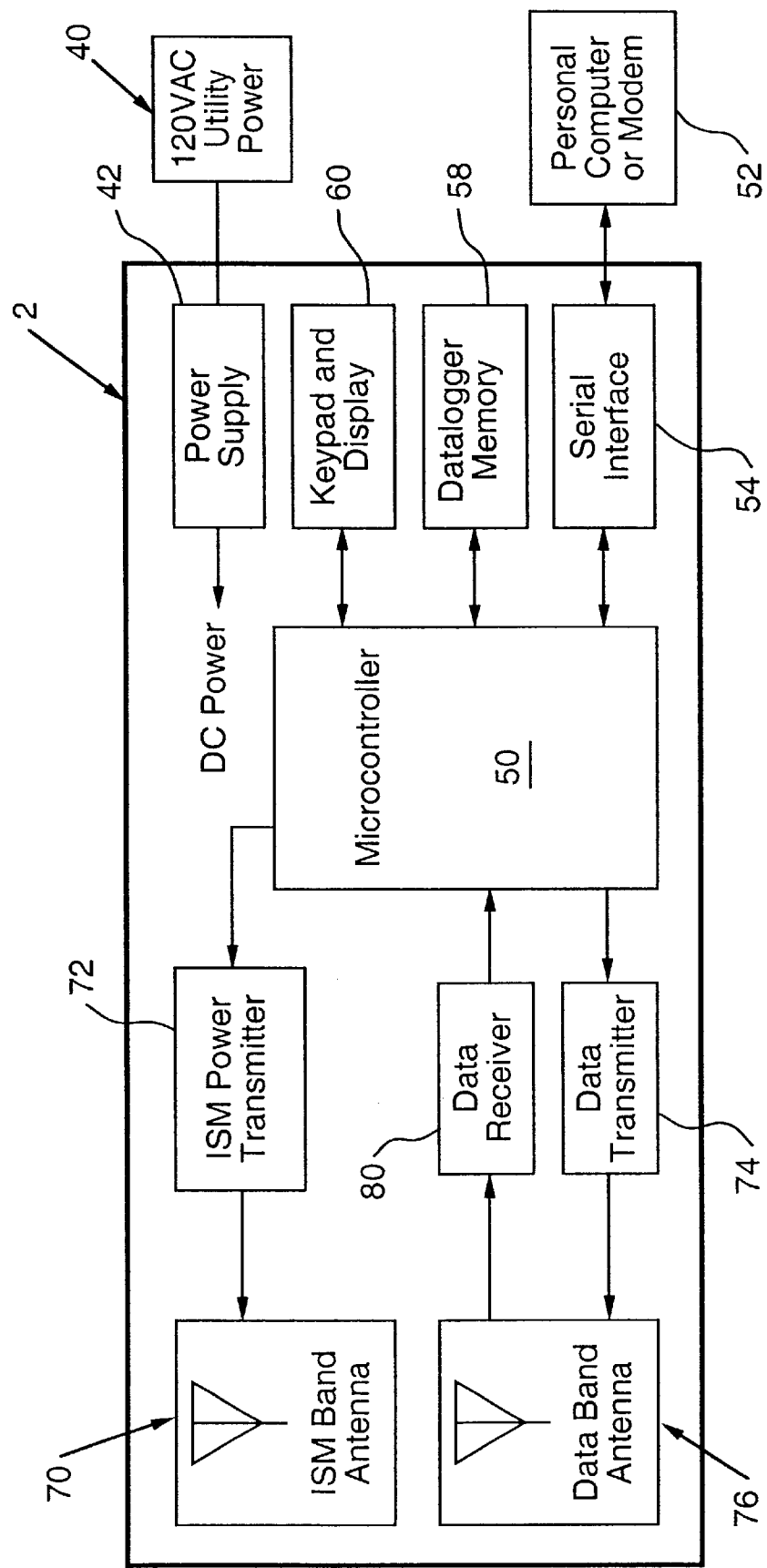
FIG. 2 is a schematic illustration of a base station usable in the present invention.

Referring to FIG. 2 in greater detail, there is shown a schematic diagram of a form of base station 2 usable in the present invention. The base station 2 is, in the form shown, energized by a 120 VAC utility power source 40, although other power sources, such as batteries, alternators and inverters, for example, may be employed, if desired. The power source is in communication with and supplies power to power supply 42 which, in turn, emits DC power at the desired level for operation of the base station 2. If desired, AC power could be employed to energize the remote station 4. A microcontroller 50, which may take the form of a microprocessor or intelligent microchip, which receives input from an analog to digital converter, a transducer employing an electronic means (such as sound, light, temperature, moisture or the like) or a program in memory, hard wired logic, an Application Specific Integrated Circuit (ASCI), from a wireless link, a satellite or cable, as in TV, for example.

A computer 52, which may be any sort of personal computer or modem if the unit is on a network, through serial interface 54 provides two-way communication with microcontroller 50. The datalogger memory 58 is in two-way communication with the microcontroller 50 and functions to provide the microcontroller 50 with any desired comparison standards, basic data, and calibration information. The keypad and display 60 is in two-way communication with microcontroller 50 and provides for keypad input into the microcontroller 50 and display of information obtained by the base station 2.

The base station 2 has an ISM (Industrial, Scientific, Medical) band antenna 70 which transmits RF signals emitted by the ISM power transmitter 72 responsive to signals received from microcontroller 50.

This serves to transmit the RF power in space to the remote station 4. In the event that light were to be the transmitted energy. The transmitted energy source may be the sun, room light, (incandescent or fluorescent) or laser light, for example. This one-way transmission is shown by the dashed arrow line 8 in FIG. 1.

The base station 2 has data transmitter 74 which has data transmitted by data band antenna 76 to the remote station 4. The data transmitted may be control, configuration, identification and processed versions of such data.

Microcontroller 50 controls data transmitter 74. Data receiver 80 receives data from the remote station 4 through data band antenna 76 and introduces the same into microcontroller 50.

It will be appreciated that in this manner the power supplied to the base station 2 not only serves to operate the base station 2, but provides the means for transmitting energy in space to remote station 4 to operate the same and transmit data to and receive data from remote station 4.

Figure 3:
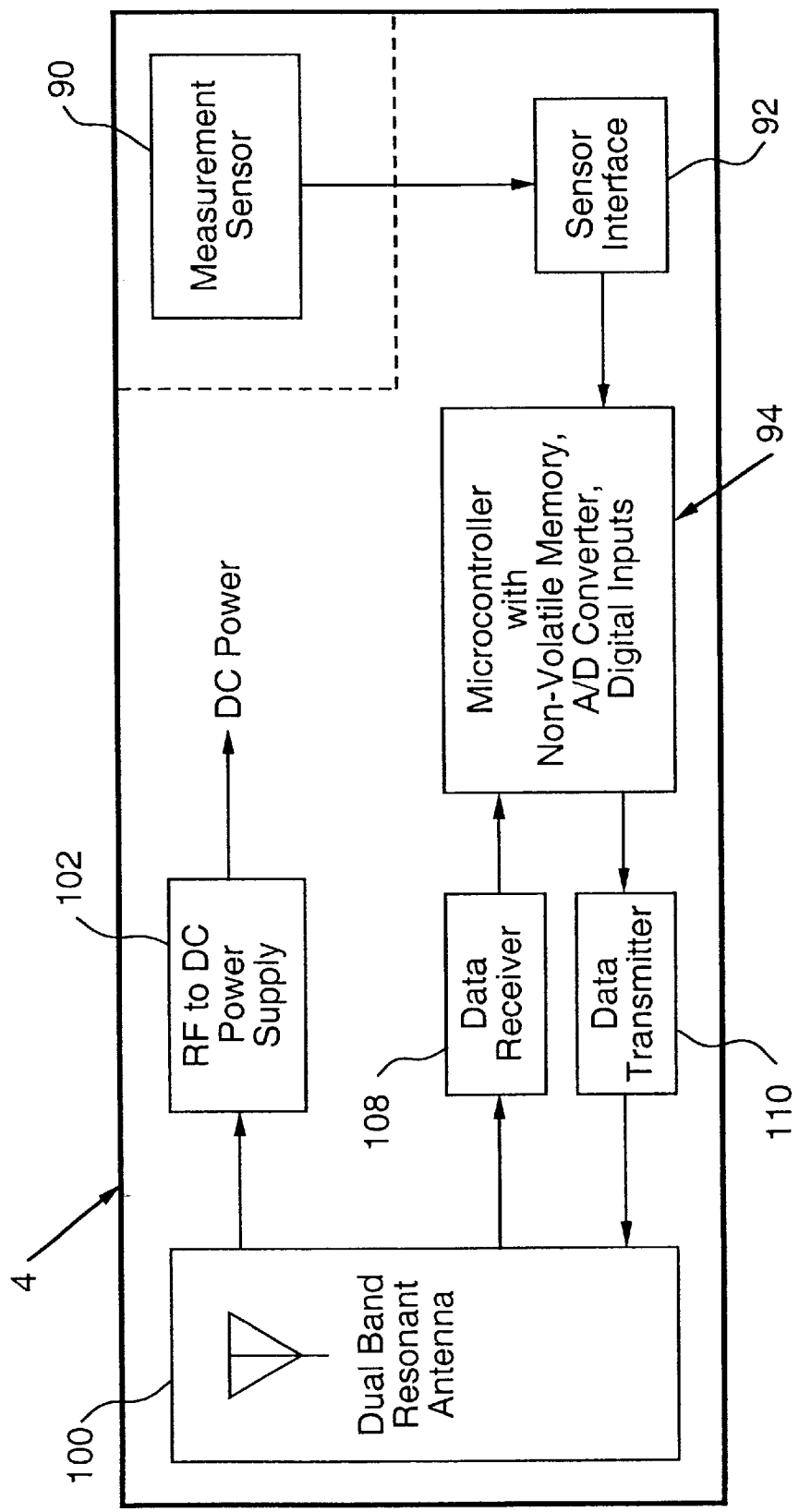
FIG. 3 is a schematic illustration of a remote station and associated sensor usable in the present invention.

Referring to FIG. 3 in greater detail, there is shown a form of remote station 4 which, in the form shown, cooperates with a measurement sensor 90 which senses an object of interest, through a sensor interface 92, interacts with microcontroller 94 which preferably has a non-volatile memory and through an analog to digital converter, direct digital measurement device or other sampling device, provides for digital input into the microcontroller 94. This microcontroller 94 controls operation of the remote station 4. A dual band resonant antenna 100 receives both the power transmissions and data transmissions from the base station 2. The power transmission is received in the converter 102, which converts the RF power to DC power, which serves to energize the remote station 4. In the alternative, a device for converting the RF power into AC power could be employed to power the remote station 4. This substitutes for the need to provide a hard wired system or to have a power storage device on the remote station. The data received from the base station 2 is delivered by the antenna 100 to data receiver 108 which, in turn, delivers the same to the microcontroller 94. This data initiates a cycle of operation of the remote station 4 and serves as the interrogation means. The data could also be data for controlling other functions such as ON/OFF switching, calibration, remote control or configuration control.

Data processed by the microcontroller 94 and received in the form shown from measurement sensor 90 is transmitted by data transmitter 110 through a double band resonant antenna 100 to base station 2 as indicated by the double-headed dashed arrow 30 in FIG. 1. It will be appreciated, therefore, that positioning of the remote station 4 with respect to the base station 2 will be heavily dependent on the application intended and will involve design of the system to provide adequate RF power and sufficient antenna capability to maintain the desired level of power for the remote station 4 and efficient communication of data between the remote station 4 and base station 2.

Numerous end use applications will be apparent to those skilled in the art. For example, in many applications the distance D in FIG. 1 will be less than 20 feet. In medical applications such as, for example, where the sensors 16, 18, 20 might be EKG sensors, a plurality of remote stations each having a sensor built into it or operatively associated therewith may be applied to the object of interest 12 which, in that case, would be a patient, such that no wires need be provided. In the alternative, in the form shown in FIG. 1, no wires need to be provided between the remote station 4 and the base station 2. Many other types of medical applications wherein sensors or information gathering apparatus is employed, such as cardiac monitors, brain monitors, pulse monitors, blood pressure monitors, oxygen monitors, as well as monitors which monitor the performance of patient support equipment, such as ventilators, intravenous delivery systems, renal dialysis machines, oxygen supplementing devices and heart bypass devices may beneficially employ the invention. Depending upon the end use, it might also be desirable to have an alarm triggered in addition to the visual presentation or computer storage or hard copy presentation of information obtained from the system.

In an alternate embodiment of the invention, uses in manufacturing processes so as to monitor equipment performance or product manufacture may advantageously find uses for the present invention. The system may also be employed for noise monitoring of equipment and providing communication for Computer Numeric Control (CNC), for example.

In some instances, where identification is desired, such as for security purposes, the remote unit might provide information to enable the base unit to confirm that an article or an individual is as represented.

In retail stores, products may have remote stations of the present invention secured thereto which at the cash register will deliver information to a base station thereby eliminating the need for bar codes and the like. This could be employed to total the charges for a specific customer as well inventory control and keep records of customer preferences.

There also may be applications involving outer space wherein the remote station provides information to an earth mounted base station.

Other uses will be apparent to those skilled in the art. A key feature is that the present system obviates the need to depend on batteries and hard wired systems as a source of energizing a remote station. Both power delivery to the remote station and two-way data transmission between the base station and the remote station are facilitated.

Figure 4:
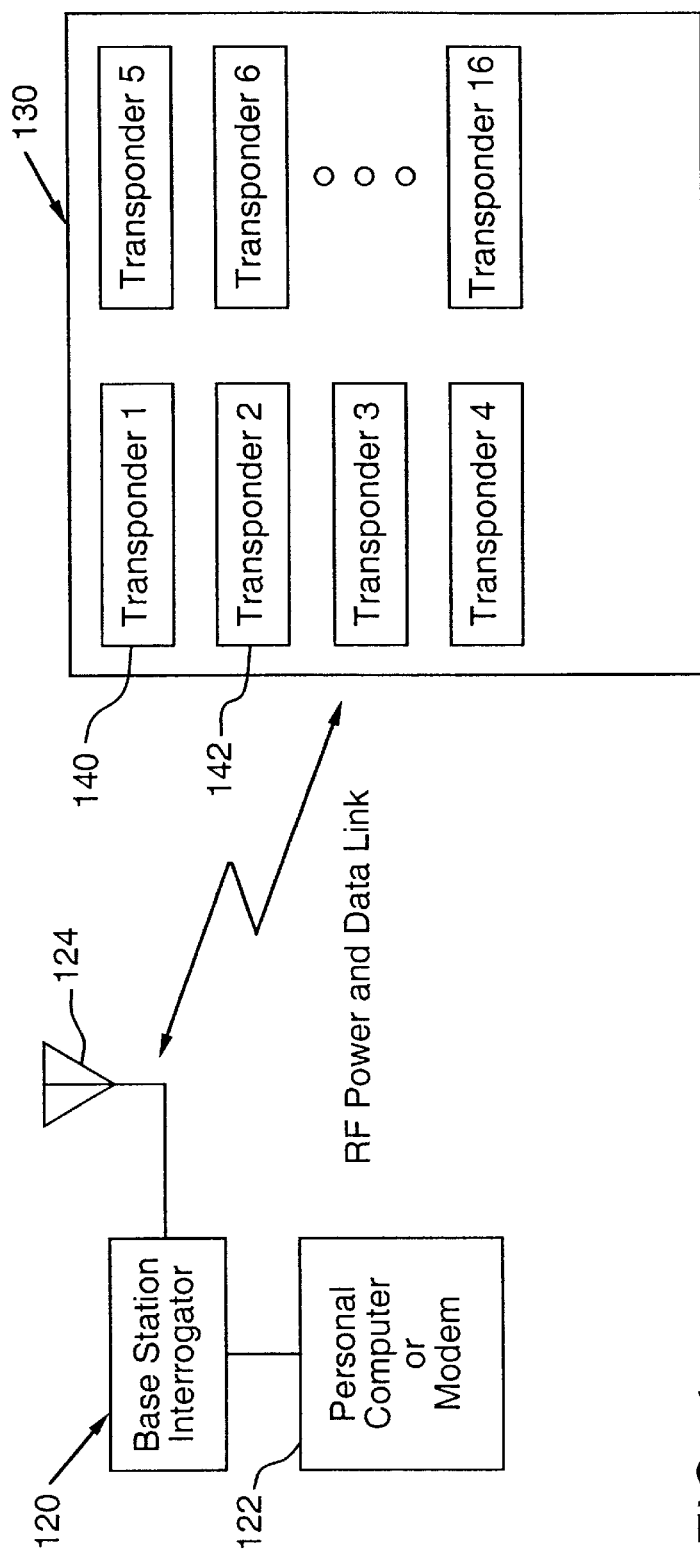
FIG. 4 is a schematic illustration of an embodiment of the present invention employing a plurality of transponders in the remote station.

Referring to FIG. 4, there is shown a system wherein the base station 120 and its associated microprocessor 122, which may be a personal computer or modem, cooperates with antenna 124 to provide for power delivery and two-way data communication with the remote station 130. As shown in FIG. 4, this embodiment contemplates the use of a plurality of transponders, such as 140, 142 which, in the form shown, total 16 in number. It is contemplated in this embodiment that each transponder will be operatively associated with a sensor receiving one type of information and will facilitate the base station sequentially interrogating each transponder 140, 142 to receive real-time information therefrom with a suitable time interval between each interrogation. Depending on the application, in lieu of sensor information, the interrogation may be to determine product codes or personal identification of an individual.

Figure 5:
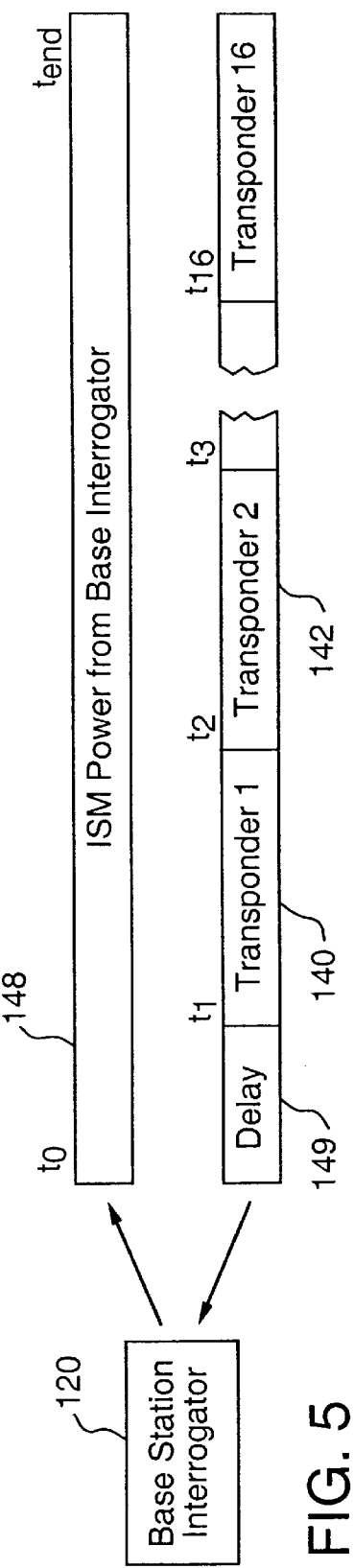
FIG. 5 is a schematic illustration of the base station interrogator and the corresponding time sequence of interrogating a plurality of transponders.

Referring to FIG. 5 there is shown a suitable communications protocol for use in the system of the present invention. The base station 120 provides means for identifying the specific transponder which is the source of the data being received and does so by polling each transponder in sequence. The power signal sent by the base station 120 may be employed as a means of providing a signal to identify the start of the polling operation. Depending upon the system address of the transponder, the data sent back will be sent at a unique time. The ISM power interrogator 148 after an initial delay period indicated generally by the reference number 149, each transponder such as transponder 140 which will be interrogated between times $t_1$ and $t_2$ and transponder 142 will be interrogated between times $t_2$ and $t_3$. In this manner, the discrete data packets received from the various transponders will be provided sequentially with identification as to source. It is preferred that a short dead time be provided between successive transponder data packets in order to avoid collisions. The data packets from the transponder may contain both sensor data and status information. The sensor data will be the information provided from the sensor through the system described hereinbefore. The status information may include information such as the specific transponder address identification, the internal DC bus voltage and, if desired, discrete digital inputs. The base interrogator will use the status information to verify the integrity of the communication links and have the capability of altering the ISM power if necessary.

Figure 6:
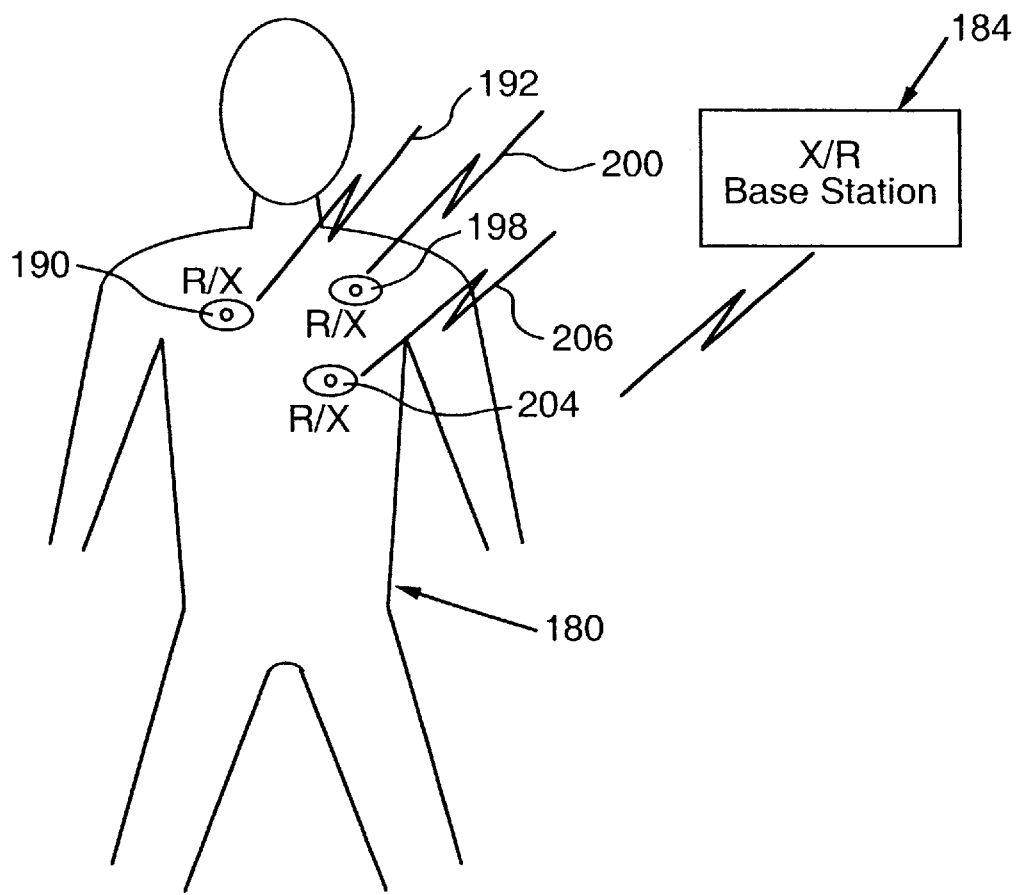
FIG. 6 is a schematic view of a plurality of electrocardiogram sensors and associated transponders, as well as the base station, which is in space communication therewith.

Referring to FIG. 6, there is shown the outline of a patient 180 with a plurality of sensors and associated remote stations 190, 198, 204, with a symbolic representation of the space communications as by RF signals 192, 200, 206 with the base station 184. In the R/X and X/R representations, the "R" indicates receiving capability and the "X" indicates transmitting capability.

Figure 7:
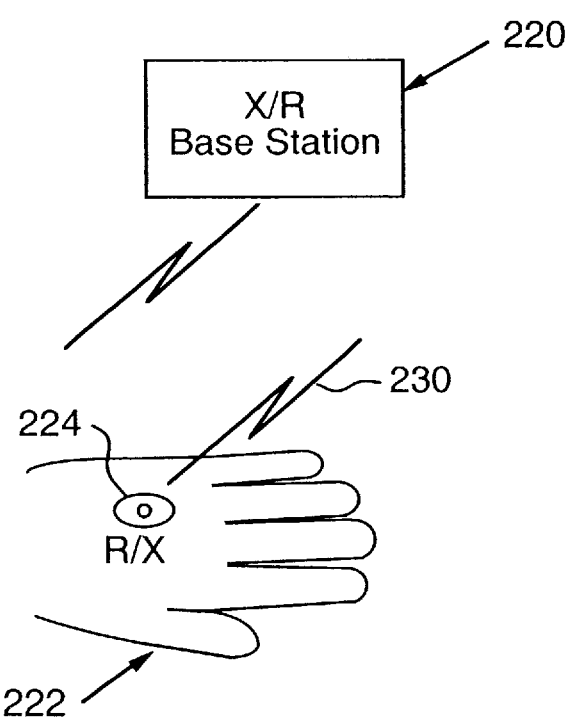
FIG. 7 is a schematic illustration of a base station in space communication with a sensor and remote station combination secured to an individual's hand to provide monitoring of the patient.

Referring to FIG. 7, there is shown a schematic of a base station 220 in space contact as by transmission of RF power shown schematically at 230 to hand 222 which contains a sensor for medical information such as pulse, blood pressure or temperature, for example, operatively associated with the remote station 224.

EXAMPLE

In order to provide additional insight into the invention an example will be provided.

A system of the type discussed in connection with FIGS. 1–3 may have a base interrogator unit or base station powered by standard commercial 120 VAC utility or equivalent UPS. If the ISM power is limited to 16 watts, then the total input power need not exceed 20 watts. The ISM power transmitter 72 will preferably be capable of outputting less than 1 watt or 1, 2, 4, 8, or 16 watts of RF energy as determined by the microcontroller 50. This will facilitate flexibility in respect of power for the program instructions and set-up parameters. An asynchronous serial port serves to connect the base station to the personal computer or modem 52 by way of an RS232 type interface. A suitable microcontroller 50 would be that marketed under the trade designation "Intel 8051." The keypad and display 60 permits users to monitor measurement data and status from the system's transponders. The keypad switches allow the user to step through a menu driven display at various parameters. The keypad may also have a password function to provide for security for restricted set up of the system parameters.

The datalogger memory 58 permits the base station to have the capability to pole multiple transponder devices in a typical system configuration. A non-volatile memory facilitates logging time stamped transponder data in a file storage buffer which can be used for data trending and uploaded by way of the serial interface 54. The non-volatile memory can be interfaced directly to the microcontroller bus as SRAM module with a real-time clock. The serial interface 54 allows connection either to a personal computer or modem. Software, firmware, ASCI or wired logic resident in the base station may include drivers for an ASCII station communication protocol in order that the system can be configured by way of a PC GUI menu system. The modem drivers will allow the base station to stand alone and accept, as well as generate telephone communications. The system firmware, non-volatile parameters and datalogger memory are all accessible by way of the serial interface 54. The power supply 42 serves to convert the 120 VAC utility input to low voltage DC to operate the control circuitry and RF transmitter. The power supply should output a well regulated 5 VDC (±5%) for the logic circuits and a 12–24 VDC output to operate the ISM power transmitter 72.

The remote station, as shown in FIG. 3, can be miniaturized and preferably has maximum dimensions of about 5 inches by 2 inches by 1 inch. The size may be reduced to the point where the remote station may implanted into the human body. One limiting factor in miniaturization is the antenna and as a result, it is preferred to raise the operating frequency as high as practical. The transponders may be about 0.5 inch in diameter and have a thickness of about 0.03215 inch.

The remote station contains no power storage device as all power is derived from the base station. Experimental results have indicated that at least 20 mw of usable DC power can be obtained in the remote station through the system described herein. The transponder has a direct-coupled analog input for interfacing with the measurement sensors. The analog to digital converter may have an input range of 0–2.5 VDC. The ISM E-field at the remote station may be approximately 3 V/m with the specific field depending upon the effective antenna gain. With respect to the telemetry link, data is returned by way of a communication link that operates outside the ISM band. The base station data receiver may have a sensitivity on the order of 0.5 uv/m. The remote station datalink RF output will generally be less than 10 mw which facilitates reliable communications over the required range. The converter serves to transform the ISM RF power into DC bus voltage on the order of 3 VDC. The RF energy coupled into the remote station antenna is an AC voltage varying at the carrier frequency. The RF to DC converter circuit rectifies and filters the RF AC voltage into a usable DC form. The rectifier and filter circuit preferably has an impedance several times lower than the overall antenna with the antenna having a characteristic impedance on the order of 377 ohms and the rectifier circuit having an impedance less than 10 ohms. A suitable microcontroller for use in the remote station is that sold under the trade designation Microchip PIC.

In a further refinement of the invention, features which are adapted for use in, but not limited to, use in miniaturized electronics and the integration of Systems on a Chip (SOC) will be considered. In such a system inherent problems regarding supplying adequate power and efficiency of communication between a base station and a remote station occur. An example of such systems is the Radio Frequency IDentification (RFID) where the device is passive with the power being supplied from a remote source which is a Radio Frequency (RF) radiator. The remote station converts the radiator RF power to DC current to drive commercially available electronics of a single chip system, for example. With increased miniaturization, the physical area of any on-board antenna or energy capturing device decreases. The present invention has structures for providing enhanced power and antennas with an effective size greater than their physical size which may advantageously be employed.

While for simplicity of disclosure, reference will be made herein to the RFID device, it will be appreciated that these features of the present invention may be employed advantageously in other systems.

An RFID device may provide a simple electronic replacement for the conventional printed bar code used in many industrial and commercial environments including customer checkout in retail stores and related inventory control. As cost is a very important item due to the bar code system being relatively inexpensive on a per item basis, the RFID tags employed on the articles as a chip attached to an antenna that is attached to a product container or product, must be competitive economically. Employing an antenna of this embodiment of the invention as an integral part CMOS (Complementary Metal Oxide Semiconductor) contributes to reduced cost of manufacture. As a result of the reduced size chips, which may be on the order of about 2.2 mm by 2.2 mm in area, for example, attention must be directed not only to enhanced power efficiency, but also the effective size of the antenna as compared with its physical size.

A feature of the embodiments is the use of a voltage doubler (charge pump) to provide sufficient voltage for certain CMOS or other fabrication technologies to function efficiently.

Figure 8:
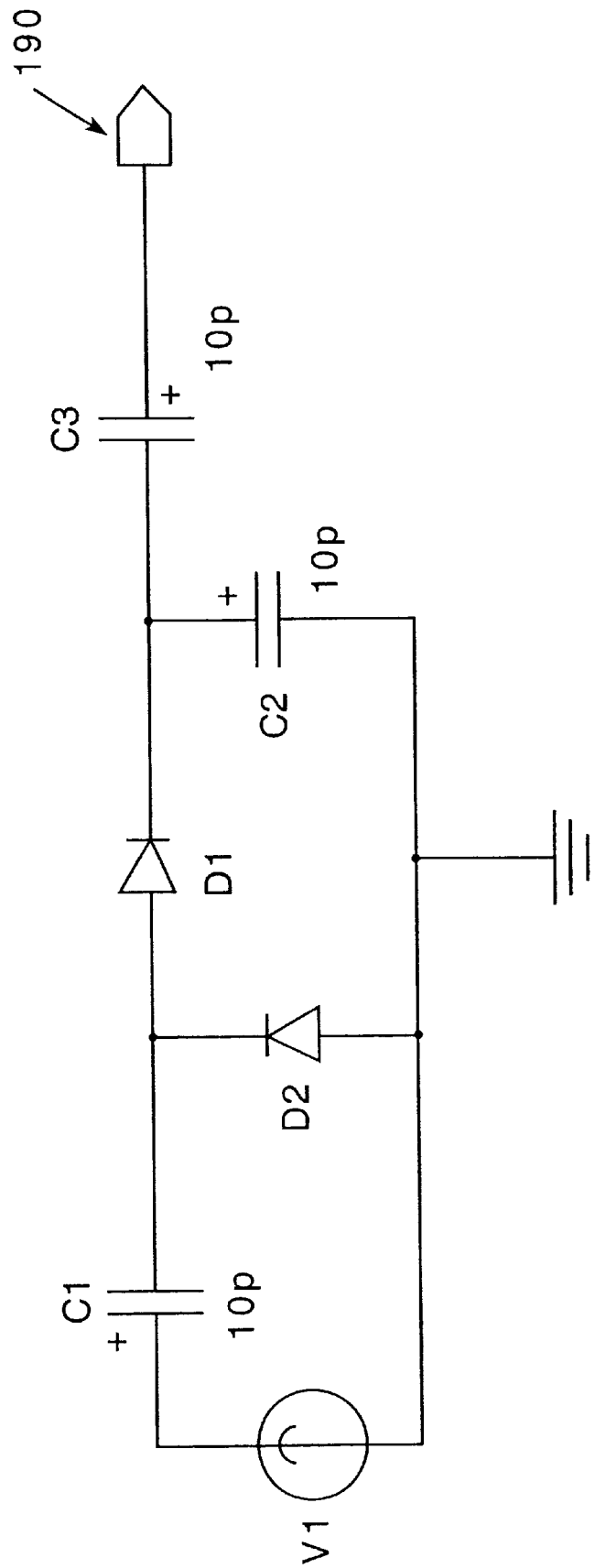
FIG. 8 is an example of a circuit of a voltage doubler on change pump of an embodiment of the invention.

With reference to FIG. 8 there is shown a voltage source V1 which represents the antenna on the remote station for receiving the RF signal. In the form shown, the circuit contains two diodes D1, D2 and three capacitors C1, C2, C3, with capacitor C1 being interposed between voltage source V1 and diodes D1 and D2. This circuit serves to increase the voltage and power emerging from output 190.

Figure 9:
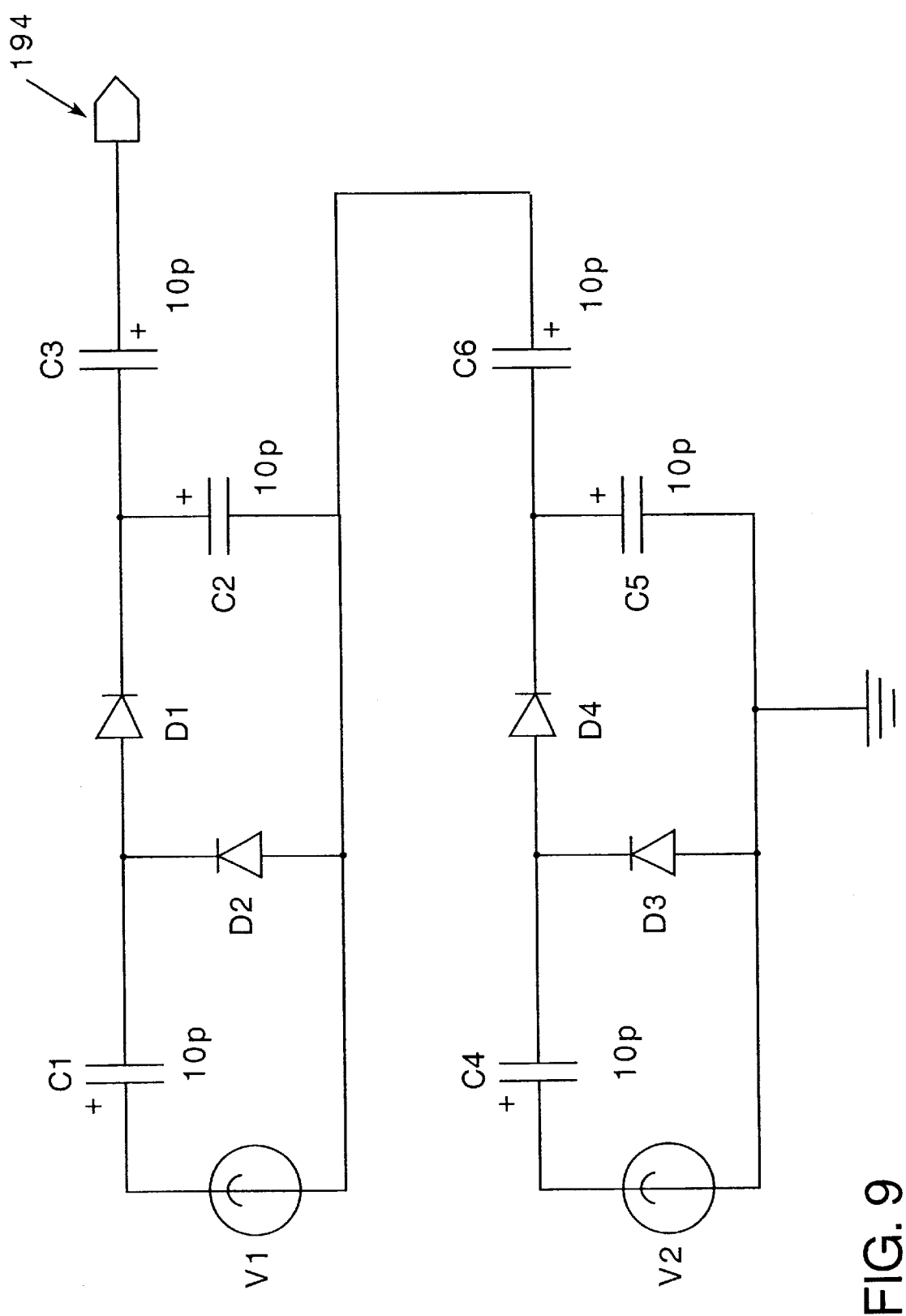
FIG. 9 is an example of a series of voltage doublers of the present invention.

The series connection of two or more voltage doublers to increase the voltage even further is exemplified in FIG. 9. The cumulative effect of voltage sources V1 and V2 provides enhanced output at 194 substantially greater than the output of the single voltage doubler in FIG. 8. The voltage sources V1 and V2 supplies are simply the two antennas with any necessary impedance matching.

Another feature of this embodiment of the invention is the use of antennas such that the effective antenna is larger than the physical antenna. The use of multiple (small) antennas in a given region to increase the energy harvest is also provided.

If the antenna efficiency is less than or equal to 50%, 2 (or more) antennas could theoretically harvest 100% of the energy. If they were of 25% efficiency, one may use 4 antennas and so on. This facilitates effecting the equivalent of the fabrication of 100% efficient antennas which, at this time, is a goal somewhat difficult to achieve.

If the antenna efficiency is greater than 50%, 2 antennas could be used with 2 different frequencies from two sources of different frequencies. This could be expanded to 3, 4, or more antennas and frequencies. A further advantage of doing this is the FCC limitation on power. If one needs 2 watts, and the maximum allowed is 1 watt at 418 MHz or 433 MHz, then one may use 2 antennas with two 1 watt transmitters satisfying the FCC and the power requirements of the device that is being powered. This is essentially a superposition of the two frequencies that theoretically could be expanded across a whole frequency band. The limitation on how many could be superimposed would be dependent on the spectrum of each transmitter and the selectivity of the tank circuit on the device receiving the energy.

Turning to the relationship between the antenna's effective area and the antenna's physical size, consider the continuous transmission of radio frequency (RF) energy from a transmitting antenna at a fixed-base location and orientation. An object of interest placed in the energy field of the transmitter scatters the incident energy possibly in many directions. Some of the energy at the object of interest is scattered in the direction of the antenna.

Consider the straight line between the "bore sight" of the transmitting antenna and the center of the object. The scattered energy in this direction is termed a monostatic scattering or the backscattering of the incident energy.

In the case of a passive object, the backscatter has an energy density that is a function of a number of factors including size, shape and composition of the object. The object is generally assumed to behave as an antenna with some effective capture area or simply effective area, $A_e$. The power reflected by this object thus acts as an antenna and is given by relationship (1), where $W_T$ is representative of the power transmitted by the source transmitting antenna; $A_e$ is the effective area of the object, and $P_R$ is the power reflected by the object.

$$P_R = A_e W_T \text{ wherein } W_T \text{ is in watts per square meter} \quad (1)$$

The device of this embodiment "harvests" the power received.

Figure 10:
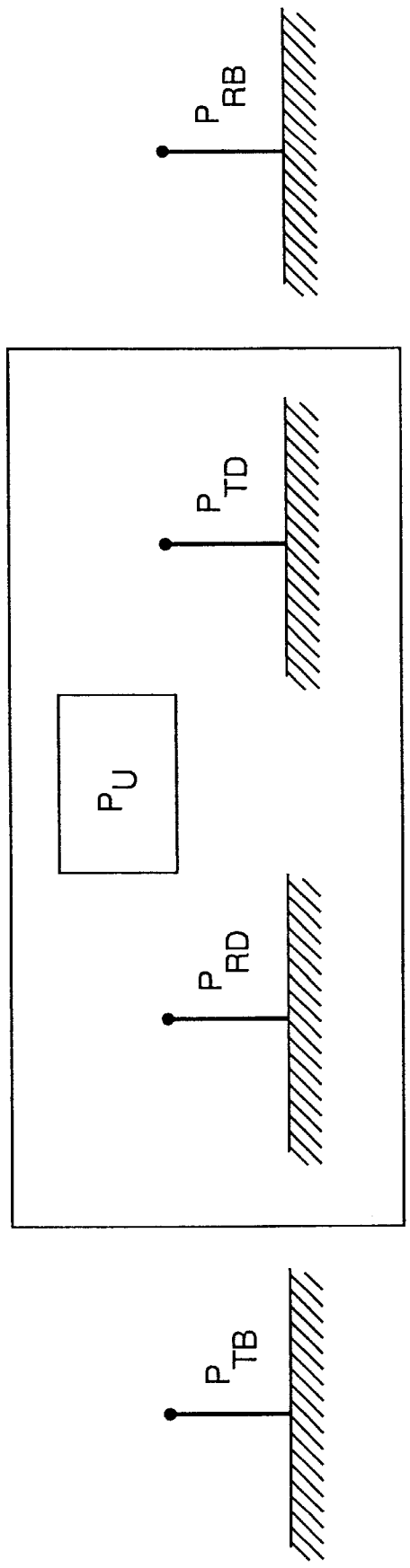
FIG. 10 is a schematic illustration of a chip on a remote station and related energy transfer.

FIG. 10 represents schematically a device for receiving, on-chip functioning and retransmission of energy. In FIG. 10, the source of power is a base station that transmits power, $P_{TB}$. The remote station device receives a certain amount of power, $P_{RD}$, uses some of the power, $P_U$, and retransmits power $P_{TD}$. A base station, $P_{RB}$, which may be collocated with the original source of power, receives the retransmitted power, Collocation would likely be the case in radar and many Radio Frequency IDentification (RFID) systems, for example.

If the function of the device is RFID, $P_{TD}$ is important to communicate information to a base station. If the function of the device (remote station) is strictly energy harvesting, $P_{TD}$ is to be minimized, i.e., maximize $P_U$. This is also the case when the device does not want to be recognized, i.e., a stealth device.

Obviously, the power leaving the device (transmitted or scattered), $P_{TD}$, is less than the incident power, $P_{RD}$. By conservation analysis, we can form equation (2).

$$P_{RD} = P_U \text{ (Power Used)} + P_{TD} \text{ (Power Transmitted/Scattered by the Device)} \quad (2)$$

For power leaving the device, the power density (watts/meter$^2$) of the transmitted or scattered power is $W_{TD}$. The subscripts used here are to maintain consistency with FIG. 10.

$$W_{TD}=[P_{RD}-P_U)/(4\pi R^2)]=[(A_e Y_0|E_{TB}|^2)/(8\pi R^2)]-[(P_U)/(4\pi R^2)]=[(A_e Y_0|E_{TB}|^2-2P_U)/(8\pi R^2)]\qquad(3)$$

In equation (3) "R" is the distance between the base station and the remote station "$Y_0$" is the admittance of free space and "$E_{TD}$" and "$E_{TB}$" the electric field strength in volts/meters. Equation (3) assumes the device is an isotropic radiator. The area, $A_e$, will be discussed hereinafter. The reflected power density from the device in the case (with $P_U=0$), $W_{TD}$, is also given where $P_U=0$:

$$W_{TD}=[(Y_0|E_{TD}|^2)/2]\qquad(4)$$

Note that WT in (4) is the incident (received) power at the device thus equating (3) and (4). In the present case, this is simply another form for the source energy density.

$$[(Y_0|E_{TD}|^2)/2]=[(A_e Y_0|E_{TB}|^2-2P_U)/(8\pi R^2)]\qquad(5)$$

$$(4\pi R^2)Y_0|E_{TD}|^2=A_e Y_0|E_{TB}|^2-2P_U\qquad(6)$$

$$A_e Y_0|E_{TB}|^2=(4\pi R^2)Y_0|E_{TD}|^2+2P_U\qquad(7)$$

$$A_e=[(4\pi R^2|E_{TD}|^2)/|E_{TB}|^2]+(2P_U)/(Y_0|E_{TB}|^2)]\qquad(8)$$

As more and more power, $P_U$, is used by the device, the ratio, $|E_{TD}|^2/|E_{TB}|^2$, will approach zero. From the standpoint of the effective area of the device, from (8), the following inequality can be seen to be true.

$$A_e\geq[(2P_U)/(Y_0|E_{TB}|^2)]\qquad(9)$$

The effective area can be calculated by measuring R, $E_T$ ($E_{TD}$) and $E_{TB}$. A remote device that (1) consumes a certain amount of the power received, $P_U$, and (2) transmits the balance of the received power, $P_{TD}$, through a second antenna on the device will be considered.

The receiving antenna on the remote device is termed the harvesting antenna, and the second antenna is termed the transmitting antenna. This type of device has been termed an Active Remote Sensor or ARS device [ARS].

Consider equation (8) in relation to inequality (9). For 100% conversion, $P_U=P_{RD}$ and $|ETD|=0$. Thus, in (8)

$$A_e=(2P_{RD})/(Y_0|E_{TB}|^2)$$

giving $$2P_{RD}=A_e Y_0|E_{TB}|^2$$

$$P_{RD}=A_e(Y_0/2)|E_{TB}|^2$$

From (1), $$P_R=P_{RD}=A_e W_T$$

substituting for WT, $$P_{RD}=A_e[Y_0|E_{TB}|^2/2]$$

which is a consistent result.

From (9), the lower bound on the effective area can be calculated by knowing the power used, $P_U$ and the field strength of the transmitted power, $|E_{TB}|^2$ The focus of this embodiment is the effective area of the harvesting antenna. The lower bound on the effective area will be considered. Jn particular, $A_e$ in (9) can be calculated simply from, $P_U$, and $|E_{TB}|$. The value to obtain in (9) is $E_{TB}$.

EXAMPLE

An antenna termed Delta 1 was fabricated using the AMI_ABN process through MOSIS [C]. The total die size was 2200 µM×2200 µM with a square spiral antenna slightly more than 3 inches in total conductor length, i.e., ¼ wavelength at 915 MHz.

Experiments were completed where the power measured at the chip, at a variety of orientations, was on the order of 5 mW. The 5 mW value was the power used, $P_U$, by the remote device (object). The electric field at the Delta 1 antenna was determined through simulation to be 55.52 volts/meter. In the relationship (9), there are three variables $A_e$, $P_U$ and $E_{TB}$.

From the experiments, we have:

(a) A $P_U$ measured value of 5 mW (b) A calculated/simulated value of $E_R$=55.52 volts/meter (c) An unknown value for $A_e$ In addition, the transmitted power, $P_{TB}$, from the base station antenna was known. From the antenna radiation pattern and the directive gain, the power density at the device antenna can be calculated.

(d) Power Density at the remote station or device=5.989 watts/meter$^2$

First, (a) and (d) were employed in a straightforward manner to determine an effective area, $A_e$, (c) assuming the energy is harvested at 100% efficiency.

$$A_e=(5\times10^{-3}\text{ watts})/(5.989\text{ watts/meter}^2)=8.349\times10^{-4}\text{ meter}^2\qquad(10)$$

Next, using (a) and (b) to determine the effective area (c).

$$A_e\geq[(2*5*10^{-3}\text{ watts})/(0.00265\text{ mhos}|E_{TB}|^2)]=12.242\times10^{-4}\text{ meter}^2\qquad(11)$$

Next, using (10) and (b), to calculate an electric field strength from (9) as a check on (b).

$$|E_{TB}|^2=(2*5*10^{-3}\text{ watts})/(0.00265\text{ mhos}*8.349\times10^{-4}\text{ meter}^2)=4519\text{ volts}^2\qquad(12)$$

$$|E_{TB}|=[4519\text{ volts}]^{1/2}=67.2\text{ volts}\qquad(13)$$

|  | Case 1 | Case 2 |
| --- | --- | --- |
| Effective area, $A_e$ | 8.349 × 10$^{-4}$ meter$^2$ | 12.242 × 10$^{-4}$ meter$^2$ |
| Electric Field Strength, $|E_{TB}|$ | 55.52 volts | 67.2 volts |

Based on the relatively close agreement of the above results, the antenna effective area is at least 8.349×10$^{-4}$ meter$^2$. From the chip dimensions, the total antenna area is actually 2.4×10.6 meter$^2$. Thus, the effective area, $A_e$, is 8.349×10$^{-4}$ meter$^2$/2.4×10$^{-6}$ meter$^2$=347.8 times the physical antenna area. (14)

From (14), it is clear that the effective area of the antenna is much greater than the physical area and within these parameters is more than 300 times greater. This facilitates effective use of the present invention on microchips on remote stations.

From the relationship in (8), it is assumed that the power used and the power radiated by the device can be considered as separable, $P_U$ and $P_{TD}$. The device is simultaneously receiving and radiating power. The received power is consumed on the device with the radiated power giving some sort of an effective area or aperture as in the case of backscatter. In essence, there are two areas involved, $A_e(P_U)$ and $Ae(P_{TD})$. There is a separability of areas, i.e., $$A_e=A_e(P_U)+A_e(P_{TD}).\qquad(15)$$

As an optimization problem, it is desirable to increase $A_e(P_U)$ and decrease $A_e(P_{TD})$. As a result, the more power used, the less of an RF signature that will be produced. However, as a stealth device, this may not be desired as the infrared (IR) signature will be increased.

In very small antennas, certain physical advantages are not gleaned from Maxwell's Equations. A ¼ wavelength whip antenna with ground plane was compared with the small die/antenna on the basis of simply physical volume occupied. The volume around the ¼ wavelength antenna and ground plane in this case occupies $1.897 \times 10^{-3}$ meter$^3$. The die/device occupies $1.473 \times 10^{-9}$ meter$^3$. As a result, the volume reduction is greater than 6 orders of magnitude. The ¼ X antenna harvests" about 50 mW of power compared to about 5 mW of power for the Delta 1 die/antenna, which is a decrease of 1 order of magnitude. The reduction in size is obviously a benefit in numerous applications.

This comparison is based on a die antenna fabricated with a CMOS process where the dielectric is strictly a function of the process available with no opportunity for size adjusting in separating the antenna from the ground plane.

The ¼ wavelength antenna used is a widely used commercial device. The Delta 1 die antenna was designed with a number of tools for producing an integrated tank circuit, but the fabrication was strictly a straightforward submission to MOSIS using the AMI-ABN 1.5μ process. The distance and dielectric between the antenna (Metal 2) and the ground plane (bottom of the silicon substrate) were not controlled. However, with this fabrication, the relative volume comparison made in FIG. 11 supports the achieving a harvest of sufficient power to perform useful functions on a CMOS or MEMS device.

Figure 11:
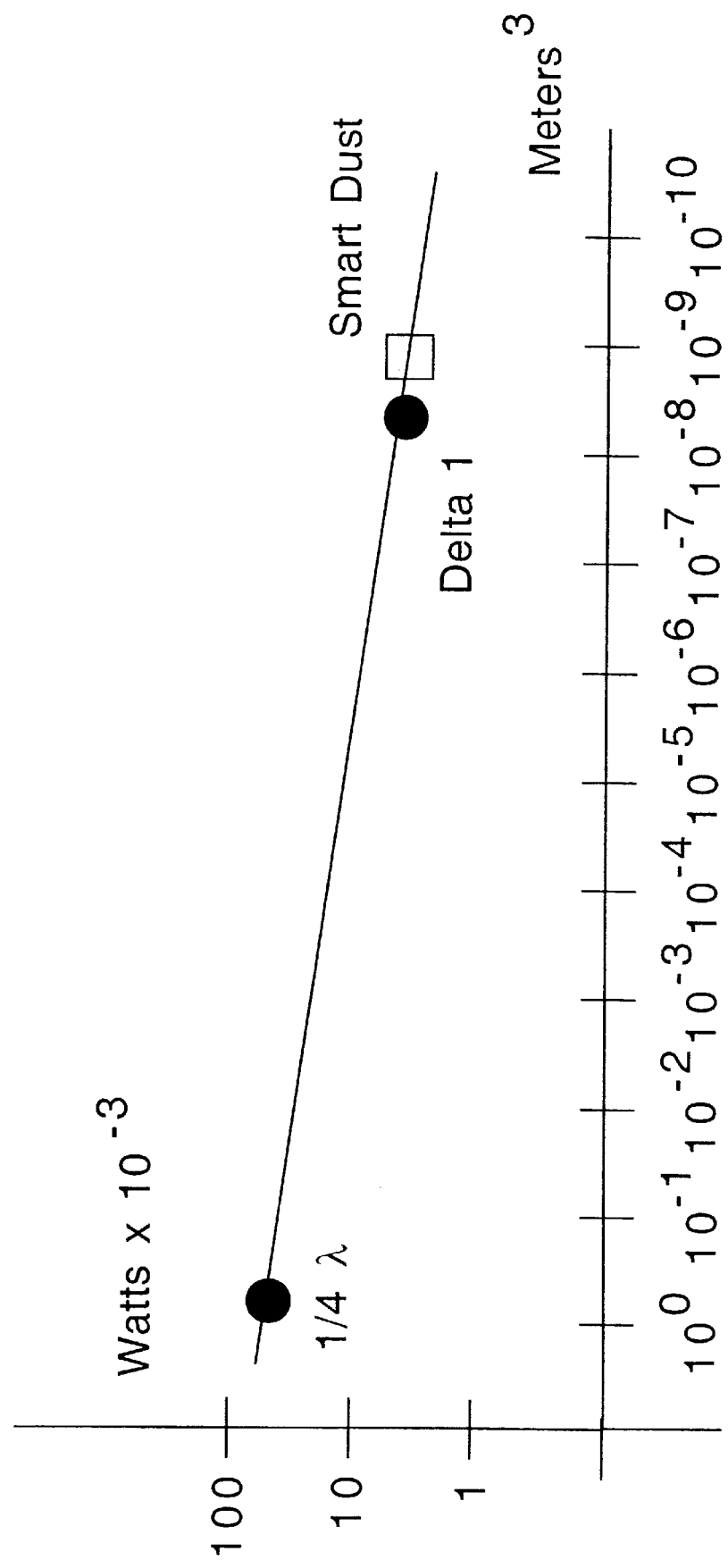
FIG. 11 is a plot of power as a function of antenna volume

Note in FIG. 11, that the Delta 1 antenna is comparable with the volume of Smart Dust when compared with the commercial antenna. Smart Dust is a combination MEMS/Electronic device on the order of 1 mm×1 mm×1 mm.

Turning again to the power enhancement through the use of a voltage doubler circuit, comparisons will be made between incident power and output voltage. Also, the use of multiple voltage doublers will be considered in further detail. Many RF products such as portable RIFD tags are too small to contain a battery. Their small demand for power, however, makes it possible to power them with ambient RF energy which may come from a base station interrogator and be captured by an antenna on the remote station. It is important, however, in converting the RF power into DC power at the remote station, to enhance the efficiency as the amount of RF energy captured by the antenna may be limited due to the antenna's relatively small size.

Figure 12B:
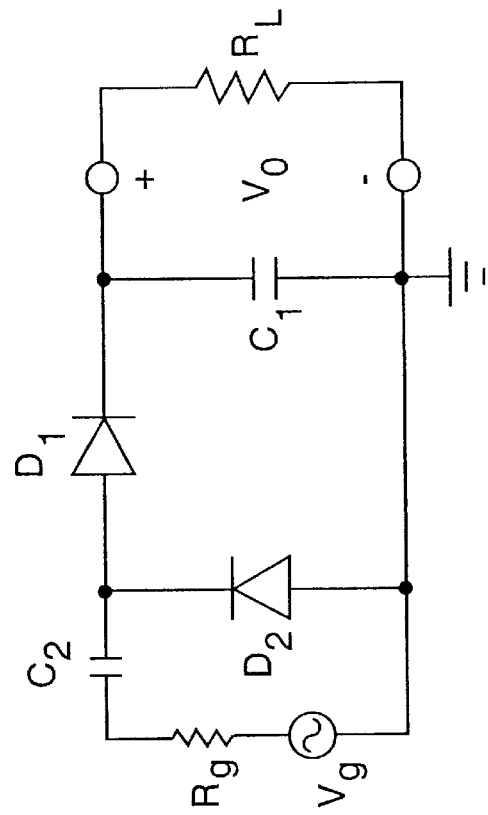
FIGS. 12(a) and 12(b) respectively show a conventional or balanced voltage doubler circuit and a cascade form of voltage doubler circuit.
Figure 12A:
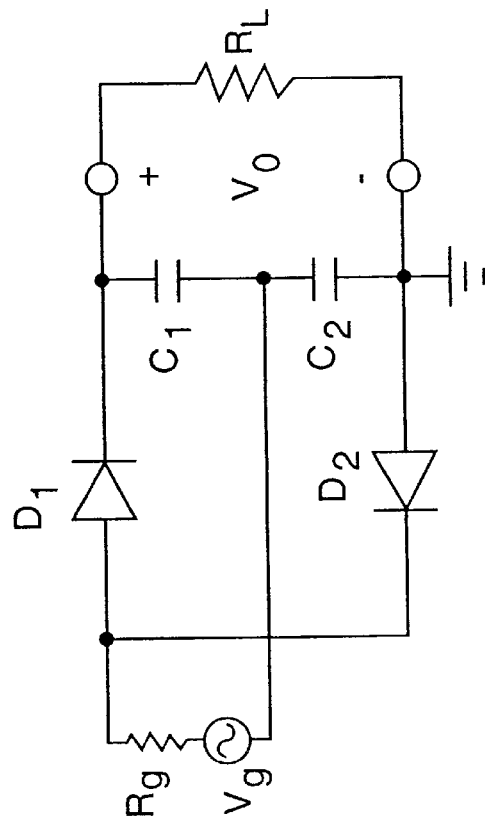

The voltage doubler presents a way of getting high DC output voltage from an AC source. It has two forms, which may be the conventional form is shown in FIG. 12(a) or the cascade form as shown in FIG. 12(b). In both forms, shown in FIGS. 12(a) and 12(b) the RF wave is rectified by $D_1$, $C_1$ in the positive cycle and by $D_2$, $C_2$ in the negative cycle. When the load $R_L$ is large, the output voltage is roughly two times the peak voltage $V_g$ of the RF source minus the turn-on voltage $V_{D0}$ of the diode.

A voltage doubler circuit, therefore, may be considered to be two single diode detector circuit in series connection.

Figure 13:
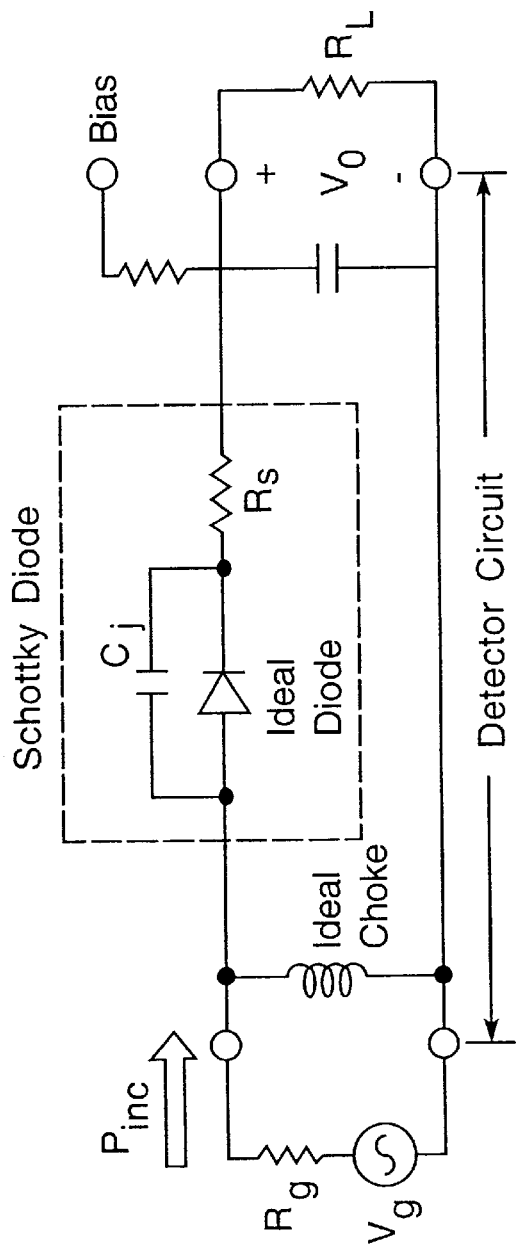
FIG. 13 illustrates a detection circuit employing a Schottky diode.

For RF applications, Schottky Diode is often employed as the detector diode as a result of its low turn-on voltage and small junction capacitance. It is modeled as an ideal exponential diode with the junction capacitance $C_J$ in series with a resistor $R_S$ as shown in FIG. 13. The ideal diode is supposed to satisfy the exponential i–v relationship.

$$i = I_s \left[ \exp\left(\frac{\Lambda v}{n}\right) - 1 \right] \tag{16}$$

wherein $I_S$ is the reverse saturation current, n is diode ideality factor, $\Lambda = q/(kT)$, q is electronic charge, k is Boltzmann's constant, T is temperature in Kelvin degrees.

It is apparent that three key parameters of the diode, $I_S$, $C_J$ and $R_S$, determine the power conversion efficiency of the voltage doubler circuit. The larger $I_S$ helps to lower down $V_{D0}$ and increases output voltage as $V_O$ is approximately equal to Vg minus $V_{D0}$. Junction capacitance diverts the diode current only to produce voltage drop on $R_S$, in order that large $C_J$ and $R_S$ will reduce the output voltage, particularly when frequencies are high. The parameters $I_S$, $C_J$ and $R_S$ are related to each other due to physical properties of the diodes.

$$I_0\left(\frac{\Lambda}{n}\sqrt{8R_g P_{inc}}\right) = \tag{17}$$
$$\left(1 + \frac{I_0}{I_S} + \frac{V_0}{R_L I_S}\right) \exp\left\{\left[1 + \frac{R_g + R_S}{R_L}\right]\frac{\Lambda}{n}V_0 + \frac{\Lambda}{n}R_S I_0\right\}$$

$I_0$ is the zero-order modified Bessel function of the first kind, $R_g$ is the source impedance, $R_L$ is the output load resistance, $I_0$ is bias circuit current for the circuit which is equal to 0 in power conversion applications.

Equation 17 describes the relationship between incident power P inc on the detector Circuit and the output voltage $V_0$.

Figure 14:
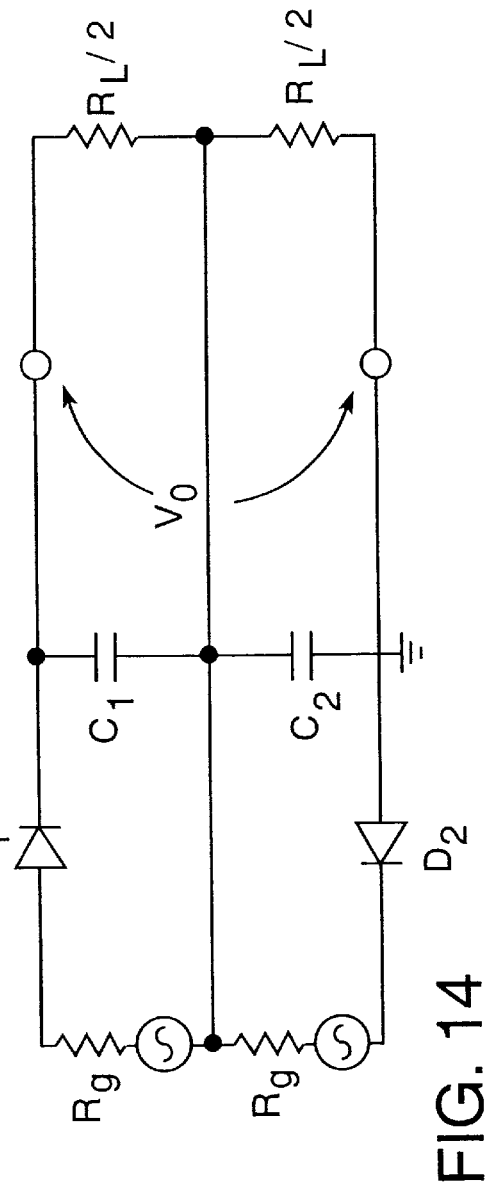
FIG. 14 is a voltage doubler equivalent circuit.

In FIG. 14, which is a voltage doubler equivalent circuit, equation 17 can be applied. It will be seen that the output voltage of the voltage doubler is two times that of a detector circuit with one half the original load.

Equation 17 is a good approximation of output voltage of a voltage doubler when $C_J$ is small or the operating frequency is low.

For some applications the output voltage of a single voltage doubler may not be adequate to operate the remote device. One may employ multiple RF sources and add them together to achieve higher output voltage. If each independent source, with the voltage double circuit dedicated to it is seen as a battery with an open circuit output voltage $V_0$ and an internal resistance $R_L$, the output voltage on a load with resistance RL will be $$V_{out} = \frac{nV_0}{nR_0 + R_L} R_L = V_0 \frac{1}{\frac{R_0}{R_L} + \frac{1}{n}} \tag{18}$$

when n of them are put together.

As seen in equation 18, the output voltage $V_{out}$ is determined by the total of capital $R_0/R_L$ and 1/n if $V_0$ is fixed. When the load is close to or smaller than the internal resistance of the voltage doubler $R_0/R_L$ becomes dominant when increasing n will not assist much in getting higher output voltage.

In summary, it is desirable to increase the $I_S$ and reduce the $C_J$ of the Schottky Diode in order to increase the power conversion efficiency of a voltage doubler. Adding multiple voltage doublers in series is a way of getting higher output voltage subject to the gain decreasing when the load becomes heavy.

Figure 15:
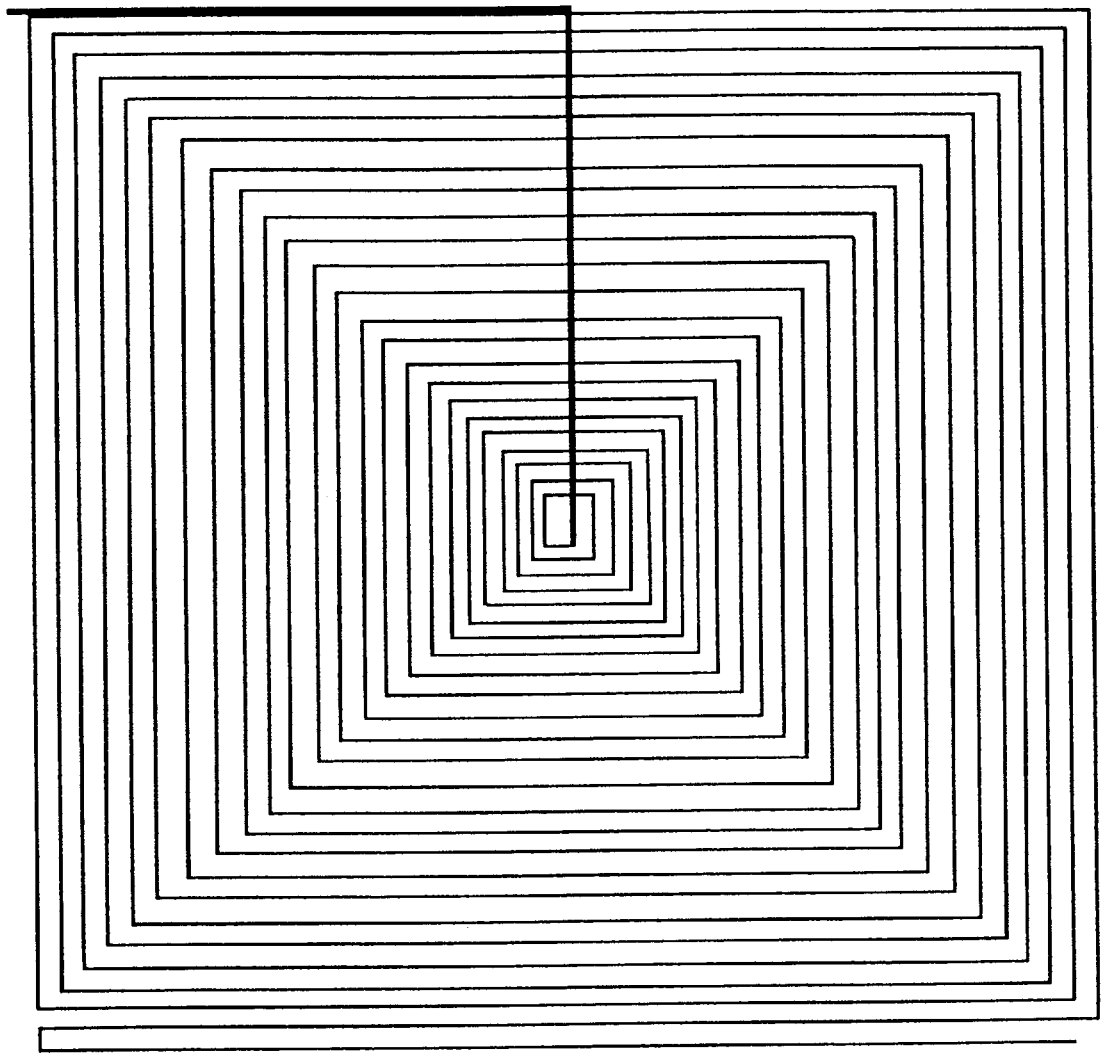
FIG. 15 is a plan view of an antenna layout for use on an electronic microchip.
Figure 16:
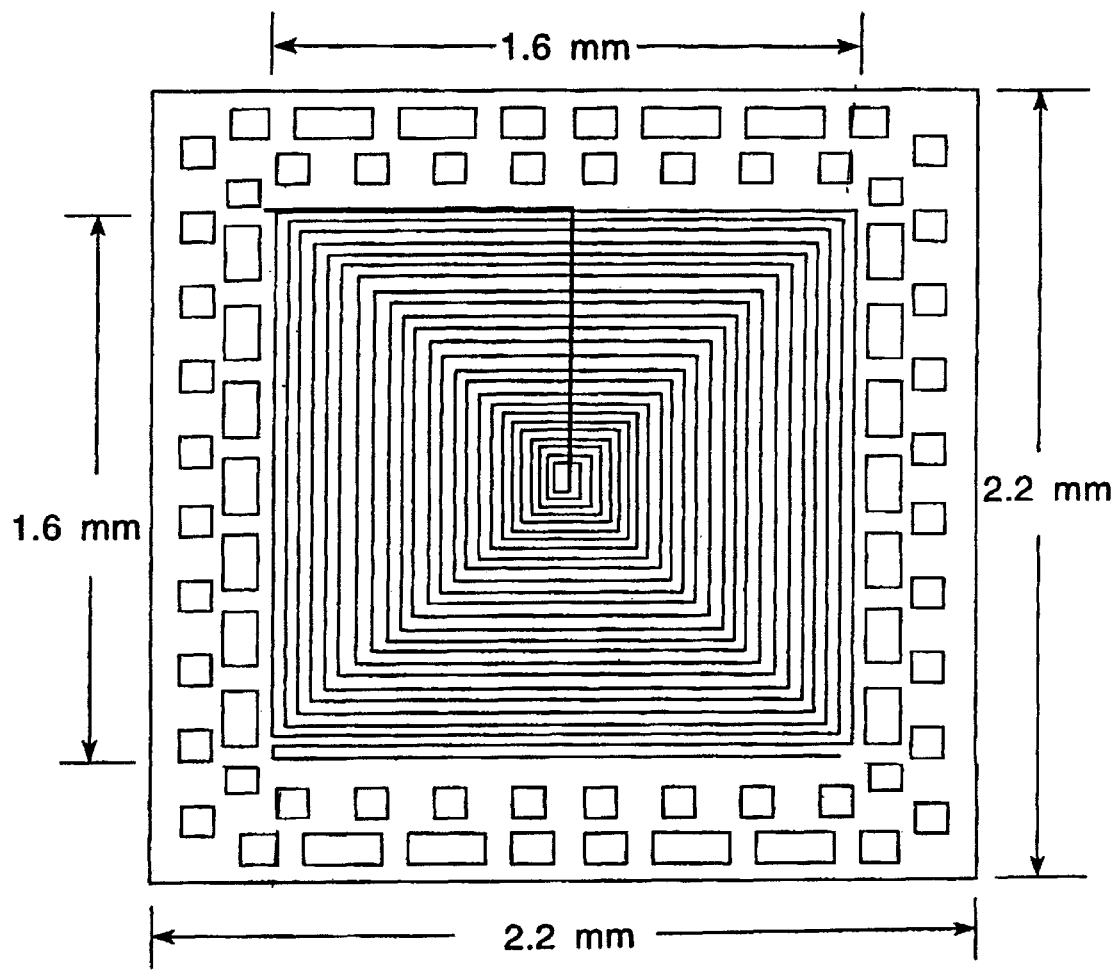
FIG. 16 is a plan view of a fabricated die chip containing an on-board antenna of the present invention.

With reference to FIG. 15, it will be noted that a further advantage of the present invention is that in connection with miniaturized electronics chips, the antenna may be provided within the rather small dimensions of the chip but have an effective antenna size greater than the physical antenna size. FIG. 15 shows such an antenna and FIG. 16 shows the antenna incorporated into an electronic microchip. Another advantage of the present system is that the system has the ability to incorporate an LC "tank" circuit in the antenna designs. This is accomplished through the use in the antenna of inter-electrode capacitance and inductance to form the LC tank circuit.

It will be appreciated, therefore, that the present invention provides an effective means for establishing a system wherein a base station cooperates with a remote station by exchanging data in both directions with the base station serving to provide transmitted energy which serves to energize the remote station to permit functioning thereof. As a result, there is no need to have a wired system connecting the remote station with a source of power or for it to carry a power storage unit. This permits low or no maintenance remote systems which may be implanted in individuals, used for other medical purposes, used in space, industry, security and a wide range of other uses. All of this is accomplished in a simple, efficient manner employing the apparatus and methods of the present invention.

While for simplicity of disclosure primary attention herein has been directed toward a system employing RF power as the source of energy delivered to the remote station, and such is currently the preferred approach, it will be appreciated that alternate sources of power may be employed. A light beam, for example, with suitable means for receiving the light on the remote station and converting it to responsive electrical output, such as an appropriate DC voltage may be employed. The converter devices, such as CMOS or TTL, could provide voltages at desired levels and currents on the order of milliamps to power the device.

Whereas particular embodiments of the invention have been described above for purposes of illustration, it will be appreciated by those skilled in the art that numerous variations of the details may be made without departing from the invention as described in the appended claims.

What is claimed is:

1. Apparatus for remote interaction with an object of interest comprising
    a remote station for obtaining information from said object of interest,
    a base station for transmitting energy in space to and communicating with said remote station,
    said remote station having conversion means for energizing said remote station responsive to receipt of said transmitted energy,
    said remote station not having a power storage device for energizing said remote station after termination of base station energy transmission to said remote station,
    first antenna means operatively associated with said base station for transmitting signals to and receiving signals from said remote station,
    second antenna means operatively associated with said remote station for receiving signals from said first antenna means and transmitting signals to said first antenna means, and
    said second antenna means having at least one antenna having an effective antenna area greater than its physical area.

2. The apparatus of claim 1 including
    said remote station having an electronic chip on which said second antenna means is formed.

3. The apparatus of claim 2 including,
    said second antenna means including a plurality of said second antennas.

4. The apparatus of claim 3 including
    at least two of said second antennas structured to receive different frequencies.

5. The apparatus of claim 4 including
    said first antenna means having a separate antenna for transmitting at each said frequency.

6. The apparatus of claim 2 including
    said base antenna having means for transmitting said energy as RF power.

7. The apparatus of claim 6 including
    said remote station having at least one voltage doubler.

8. The apparatus of claim 7 including
    said remote station having at least two said voltage doublers in series.

9. The apparatus of claim 7 including
    each said voltage doubler having at least one capacitor electrically interposed between said second antenna means and a diode.

10. The apparatus of claim 3 including,
    said second antennas formed on said electronic chip.

11. The apparatus of claim 10 including
    an LC link circuit formed in said second antenna means.

12. The apparatus of claim 2 including
    said remote station is an RFID tag.

13. The apparatus of claim 2 including said chip is a device selected from the group of a CMOS device and a MEMS device.

14. The apparatus of claim 2 including a power supply for energizing said base station.

15. The apparatus of claim 2 including
    first controller means for controlling operation of said base station.

16. The apparatus of claim 15 including
    said first controller means having microprocessor means.

17. The apparatus of claim 2 including
    said remote station having converter means for converting said RF power into DC or AC power.

18. The apparatus of claim 1 including
    said effective antenna area is at least 300 times the antenna's physical area.

19. The apparatus of claim 1 including
    said remote station having means for converting said transmitted energy into DC power for energizing said remote station.

20. The apparatus of claim 19 including
    said remote station having second controller means for processing information received from said base station and for transmitting information to said base station.

21. The apparatus of claim 20 including
    said second controller means having means for receiving information from sensor means monitoring said object of interest.

22. The apparatus of claim 20 including
    said object of interest being a patient.

23. The apparatus of claim 22 including
    said sensor means having apparatus to monitor a body condition or body function of said patient.

24. The apparatus of claim 19 including
    said base station transmitting both power signals and data signals to said remote station.

25. The apparatus of claim 1 including
said remote station not having a power storage device physically secured thereto.

26. The apparatus of claim 1 including
said base station and said remote station having no wired connection therebetween.

27. The apparatus of claim 1 including
said remote station being sealed within a resinous plastic material.

28. A method for remote interaction with an object of interest comprising
providing a remote station and a base station operatively associated therewith,
transmitting energy in space from said base station to said remote station,
converting said energy received by said remote station into electrical power to energize said remote station,
effecting said energy received by said remote station into electrical power to energize said remote station,
effecting said remote interaction without requiring such remote station to have a power storage device secured thereto for energizing said remote station after termination of said base station transmission and said energy conversion,
employing antenna means for communication of said electrical power in space between said base station and said remote station,
said antenna means having first antenna means operatively associated with said base station and second antenna means operatively associated with said remote station, and
said second antenna means having at least one antenna having an effective antenna area greater than the physical area.

29. The method of claim 28 including
said remote station employing an electronic chip on which said second antenna means is formed.

30. The method of claim 29 including
employing a plurality of second antennas as said second antenna means.

31. The method of claim 30 including
at least two of said second antennas structured to receive different frequencies.

32. The method of claim 31 including
said first antenna means having antennas for transmitting at each said frequency.

33. The method of claim 30 including
said second antennas formed on said electronic chip.

34. The method of claim 33 including
providing an LC link circuit in said second antenna.

35. The method of claim 34 including
employing said method to confirm identification of an object of interest.

36. The method of claim 35 including
employing said method in a security system.

37. The method of claim 29 including
transmitting said energy from said base station as RF power.

38. The method of claim 37 including
employing in said remote station at least one voltage doubler.

39. the method of claim 38 including
employing in said remote station at least two said voltage doublers in series.

40. The method of claim 38 including
providing in each said voltage doubler at least one capacitor electronically interposed between said second antenna means and a diode.

41. The method of claim 40 including
employing a said remote station not having a power storage device.

42. The method of claim 41 including
employing first microprocessor means to control operation of said base station.

43. The method of claim 42 including
employing second microprocessor means to control said remote station.

44. The method of claim 29 including
employing as said remote station an RFID tag.

45. The method of claim 29 including
employing as said chip a device selected from type group consisting of a CMOS device and a MEMS device.

46. The method of claim 28 including
transmitting said energy as RF power.

47. The method of claim 28 including
said effective antenna area is at least 300 times the antennas physical area.

48. The method of claim 28 including
energizing said base station by a power supply.

49. The method of claim 48 including
converting said transmittal energy to DC power at said remote station.

50. The method of claim 28 including
employing said method on an object of interest which is a patient.

51. The method of claim 50 including
employing said method to monitor a body condition or body function of said patient.

52. The method of claim 50 including
positioning said remote station within 20 feet of said base station.

53. The method of claim 28 including
sealing said remote station within a resinous plastic material.

54. The method of claim 28 including
transmitting both power signals and data signals from said base station to said remote station.

55. The method of claim 54 including
transmitting data signals from said remote station to said base station.

* * * * *